United States Patent
Park et al.

(10) Patent No.: US 6,741,885 B1
(45) Date of Patent: May 25, 2004

(54) IMPLANTABLE CARDIAC DEVICE FOR MANAGING THE PROGRESSION OF HEART DISEASE AND METHOD

(75) Inventors: Euljoon Park, Stevenson Ranch, CA (US); Eric Falkenberg, Simi Valley, CA (US); Gene A. Bornzin, Simi Valley, CA (US); Junyu Mai, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 378 days.

(21) Appl. No.: 09/908,179

(22) Filed: Jul. 17, 2001

Related U.S. Application Data

(60) Provisional application No. 60/254,068, filed on Dec. 7, 2000.

(51) Int. Cl.[7] ............................... A61B 5/04
(52) U.S. Cl. ................ 600/509; 600/529; 607/19; 607/20
(58) Field of Search ................ 600/509, 529; 607/19, 20, 32

(56) References Cited

U.S. PATENT DOCUMENTS

| | | | |
|---|---|---|---|
| 4,702,253 A | 10/1987 | Nappholz et al. | 128/419 |
| 4,716,887 A | 1/1988 | Koning et al. | 128/419 |
| 4,815,469 A | 3/1989 | Cohen et al. | 128/634 |
| 4,901,725 A | 2/1990 | Nappholz et al. | 128/419 |
| 5,020,541 A | 6/1991 | Marriott | 128/723 |
| 5,113,869 A | 5/1992 | Nappholz et al. | 128/696 |
| 5,140,045 A | 8/1992 | Askanazi et al. | 514/561 |
| 5,197,467 A | 3/1993 | Steinhaus et al. | 128/419 |
| 5,201,808 A | 4/1993 | Steinhaus et al. | 128/419 |
| 5,383,473 A | 1/1995 | Moberg | 128/782 |
| 5,396,893 A | 3/1995 | Oberg et al. | 128/671 |
| 5,425,750 A | 6/1995 | Moberg | 607/19 |
| 5,454,838 A | 10/1995 | Vallana et al. | 607/19 |

(List continued on next page.)

FOREIGN PATENT DOCUMENTS

| | | | |
|---|---|---|---|
| DE | 25 27 475 A1 | 12/1976 | A61B/5/00 |
| FR | 2 664 487 A1 | 1/1992 | A61B/5/02 |
| WO | WO 86/07248 | 5/1986 | A61B/5/02 |

OTHER PUBLICATIONS

Park, E., Assessment of Heart Failure Using Stimulation Device–Based Activity Sensor, Journal of Cardiac Failure, vol. 6, No. 3, Supplement 2, pp: 43, No. 163 (Sep. 2000).

Medtronic Chronicle, Medtronic, Inc., "Medtronic Announces Two Major Milestones in its Effort to Treat Patients with Heart Failure", Aug. 18, 1998, pp. 1–2.

Cohen, et al., "A Hemodynamically Responsive Antitachycardia System", Circulation, vol. 82, No. 2, Aug. 1990, pp. 394–406.

Medtronic Chronicle, Medtronic, Inc., "Reveal Insertable Loop Recorder System", 1998, 6 pages.

Turcott et al., "Fractal Character of the Electrocardiogram: Distinguishing Heart–Failure and Normal Patients", Annals of Biomedical Engineering, vol. 24, 1996, pp. 269–293.

*Primary Examiner*—Mark Bockelman

(57) ABSTRACT

An implantable cardiac device detects a progression or regression in heart disease such as congestive heart failure. An activity sensor and a respiration sensor generate raw signals indicative of the patient's activity level and respiration level. Degradation or improvement of the patient's activity and respiration over a predetermined time corresponds to an indication of the progression or regression of the heart disease. A processor coupled to the sensors is programmed to process the raw sensor signals over the predetermined time and stores the processed sensor signals in a memory having a data storage area. A telemetry circuit coupled to the memory is configured to transmit the stored sensor signals to an external monitor for subsequent display. The processor further controls pacing of the heart, adjusts pacing therapy responsive to the process signals, and process the raw respiration signals when the patient is in a number of different active states.

139 Claims, 8 Drawing Sheets

U.S. PATENT DOCUMENTS

| | | | |
|---|---|---|---|
| 5,476,483 A | 12/1995 | Bornzin et al. | 607/17 |
| 5,487,753 A | 1/1996 | MacCarter et al. | 607/17 |
| 5,496,351 A | 3/1996 | Plicchi et al. | 607/17 |
| 5,514,162 A | 5/1996 | Bornzin et al. | 607/19 |
| 5,549,650 A | 8/1996 | Bornzin et al. | 607/24 |
| 5,562,711 A | 10/1996 | Yerich et al. | 607/17 |
| 5,605,151 A | 2/1997 | Lynn | 128/633 |
| 5,738,102 A | 4/1998 | Lemelson | 128/671 |
| 5,792,197 A | 8/1998 | Nappholz | 607/17 |
| 5,862,803 A | 1/1999 | Besson et al. | 128/696 |
| 5,876,353 A | 3/1999 | Riff | 600/547 |
| 5,935,081 A | 8/1999 | Kadhiresan | 600/513 |
| 5,957,861 A | 9/1999 | Combs et al. | 600/547 |
| 5,974,340 A | 10/1999 | Kadhiresan | 607/18 |
| 6,021,351 A | 2/2000 | Kadhiresan et al. | 607/19 |
| 6,045,513 A | 4/2000 | Stone et al. | 600/508 |
| 6,104,949 A | 8/2000 | Pitts Crick et al. | 600/547 |
| 6,135,966 A | 10/2000 | Ko | 600/481 |
| 6,264,606 B1 | 7/2001 | Ekwall et al. | 600/300 |
| 6,264,611 B1 | 7/2001 | Ishikawa et al. | 600/486 |
| 6,275,727 B1 | 8/2001 | Hopper et al. | 600/513 |
| 6,409,675 B1 | 6/2002 | Turcott | 600/508 |
| 6,438,408 B1 | 8/2002 | Mulligan et al. | 600/510 |
| 6,454,719 B1 | 9/2002 | Greenhut | 600/484 |
| 6,459,929 B1 | 10/2002 | Hopper et al. | 600/513 |

IMPLANTABLE CARDIAC DEVICE FOR MANAGING THE PROGRESSION OF HEART DISEASE AND METHOD

This application claims the benefit of U.S. Provisional Application No. 60/254,068, filed Dec. 7, 2000.

FIELD OF THE INVENTION

The present invention is generally directed to an implantable stimulation device for monitoring the progression or regression of heart disease and modifying stimulation in response thereof. The present invention is more particularly directed to such a device which monitors one or more physiological parameters of a patient, over an extended time period, indicative of the progression or regression of congestive heart failure.

BACKGROUND OF THE INVENTION

Congestive heart failure (CHF) is a debilitating, end-stage disease in which abnormal function of the heart leads to inadequate blood flow to fulfill the needs of the body's tissues. Typically, the heart loses propulsive power because the cardiac muscle loses capacity to stretch and contract.

Often, the ventricles do not adequately fill with blood between heartbeats and the valves regulating blood flow may become leaky, allowing regurgitation or back flow of blood. The impairment of arterial circulation deprives vital organs of oxygen and nutrients. Fatigue, weakness, and inability to carry out daily tasks may result.

Not all CHF patients suffer debilitating symptoms immediately.

Some may live actively for years. Yet, with few exceptions, the disease is relentlessly progressive.

As CHF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an attempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

CHF has been classified by the New York Heart Association (NYHA). Their classification of CHF corresponds to four stages of progressively worsening symptoms and exercise capacity from Class I to Class IV. Class I corresponds to no limitation wherein ordinary physical activity does not cause undue fatigue, shortness of breath, or palpitation. Class II corresponds to slight limitation of physical activity wherein such patients are comfortable at rest, but where ordinary physical activity results in fatigue, shortness of breath, palpitations, or angina. Class III corresponds to a marked limitation of physical activity wherein, although patients are comfortable at rest, less than ordinary activity will lead to symptoms. Lastly, Class IV corresponds to inability to carry on any physical activity without discomfort, wherein symptoms of CHF are present even at rest and where with any physical activity, increased discomfort is experienced.

Current standard treatment for heart failure is typically centered around medical treatment using ACE inhibitors, diuretics, and digitalis. It has also been demonstrated that aerobic exercise may improve exercise tolerance, improve quality of life, and decrease symptoms. Only an option in 1 out of 200 cases, heart transplantation is also available. Other cardiac surgery is also indicated for only a small percentage of patients with particular etiologies. Although advances in pharmacological therapy have significantly improved the survival rate and quality of life of patients, patients in NYHA Classes III or IV, who are still refractory to drug therapy, have a poor prognosis and limited exercise tolerance. Cardiac pacing has been proposed as a new primary treatment for patients with drug-refractory CHF.

By tracking the progression or regression of CHF more closely, treatments could be administered more effectively. Commonly, patients adapt their lifestyle and activities to their physical condition. The activity level of the patients with NYHA Class III or IV would be much lower than that of the patients with NYHA Class I or II. The change in lifestyle or activity level, due to the patient's heart condition, will be reflected by activity and respiration physiological parameters.

The present invention addresses the issues of tracking CHF progression or regression to enhance the administration of therapies and to enable the monitoring of the effectiveness of such therapies.

SUMMARY OF THE INVENTION

The present invention provides an implantable cardiac device for detecting a progression or regression in heart disease such as congestive heart failure. An activity sensor generates raw sensor signals indicative of the patient's activity level. Degradation or improvement of the patient's activity level over a predetermined extended time corresponds to an indication of the progression or regression of the heart disease. A processor processes the raw sensor signals over the predetermined extended time and determines relative changes in activity levels. A memory having a data storage area stores the activity levels during the predetermined extended time and a telemetry circuit transmits the activity levels to an external monitor for display.

The activity measurements are taken at frequent intervals. The processor at time intervals such as once per day stores selected activity levels in the memory. The selected activity levels stored may, for example, represent a maximum change in activity level recorded during the last 24 hours.

Similarly, a respiration sensor generates raw sensor signals indicative of the patient's respiration. Degradation or improvement of the patient's respiration levels over the predetermined extended time further corresponds to an indication of progression or regression of the heart disease. The processor processes the raw respiration sensor signals to determine respiration levels. The respiration levels are preferably frequently determined for updating previously stored respiration levels in the memory. At the end of the time interval, for example every 24 hours, the processor samples selected respiration levels and stores the selected respiration levels in the memory. The selected respiration levels may represent maximum and minimum values corresponding to selected respiration parameters.

At the end of the predetermined extended time which may be, for example, 24 weeks, the activity and respiration parameters for each day of the last 24 weeks are available in the memory to be transmitted to the external monitor for display. The memory is preferably configured to be a circulating memory so that at any time the selected daily stored activity and respiration levels over the last 24 weeks are available for transmission to the external monitor for display.

In accordance with further aspects of the present invention, the processor maintains a histogram of activity and respiration levels. This histogram is updated at frequent intervals such as every 30 seconds. At the end of a time period as, for example, at the end of each week, the processor derives from the histogram a set of histogram values which are then stored in the memory. The histogram values stored each week may be maintained by the memory over the predetermined extended time of, for example, 24 weeks.

The activity parameters stored in the memory at the end of the time intervals as, for example, each day, in accordance with the present invention, include active time count which represents the longest duration of the activity being larger than the long-term activity average level, maximum activity variance level representing the maximum activity variance recorded during the last 24 hours, maximum activity taken from the activity histogram, and median and mode activity variance taken from an activity variance histogram. The respiration levels which are stored in the memory after each 24-hour period, in accordance with further aspects of the present invention, may be the maximum values for respiration rate, tidal volume and minute ventilation during sustained exercise episodes, base-line respiration rate, tidal volume and minute ventilation during normal respiration in resting condition, respiration rate, tidal volume and minute ventilation during abnormal respiration such as cyclic breathing, hyper and hypo ventilation periods, a single cyclic breathing period, total duration, total number of cyclic breathing, total time in cyclic breathing, and total time in normal sleep. The respiration levels, in accordance with the present invention, are derived from impedance levels made by the respiration sensor.

The histograms maintained in the memory by the processor preferably comprise three histograms. One histogram provides an historical record of recent activity levels of the patient. Another histogram provides an historical record of the activity variance of the patient and a third histogram provides an historical record of the difference between short-term respiration levels and long-term respiration levels of the patient. After the histogram values are determined by the processor, the histograms are cleared. As a result, at any time, the memory will contain histogram values taken each week over a 24-week period.

The foregoing provides a comprehensive history of the patient's activity and respiration levels over an extended period of time. While the recorded levels made available for display are comprehensive in nature, only limited memory space is required for holding the most recent parameters for an extended period of 24 weeks. Upon display of the recorded levels, the progression or regression of the heart disease may be readily determined.

In accordance with a further aspect of the present invention, when the device is a cardiac rhythm management device for delivering therapy, such as pacing therapy to the patient's heart, the device itself may adjust therapy responsive to the determined physiological parameter levels. The therapy adjustment may take the form, for example, of pacing rate adjustments to assist the patient in breathing or in the removal of fluid from the lungs.

In accordance with a further aspect of the present invention, the respiration measurements are taken during different patient activity conditions. To that end, when it is time to take and update respiration levels, the respiration and activity measurements stored are determined by the patient activity condition.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
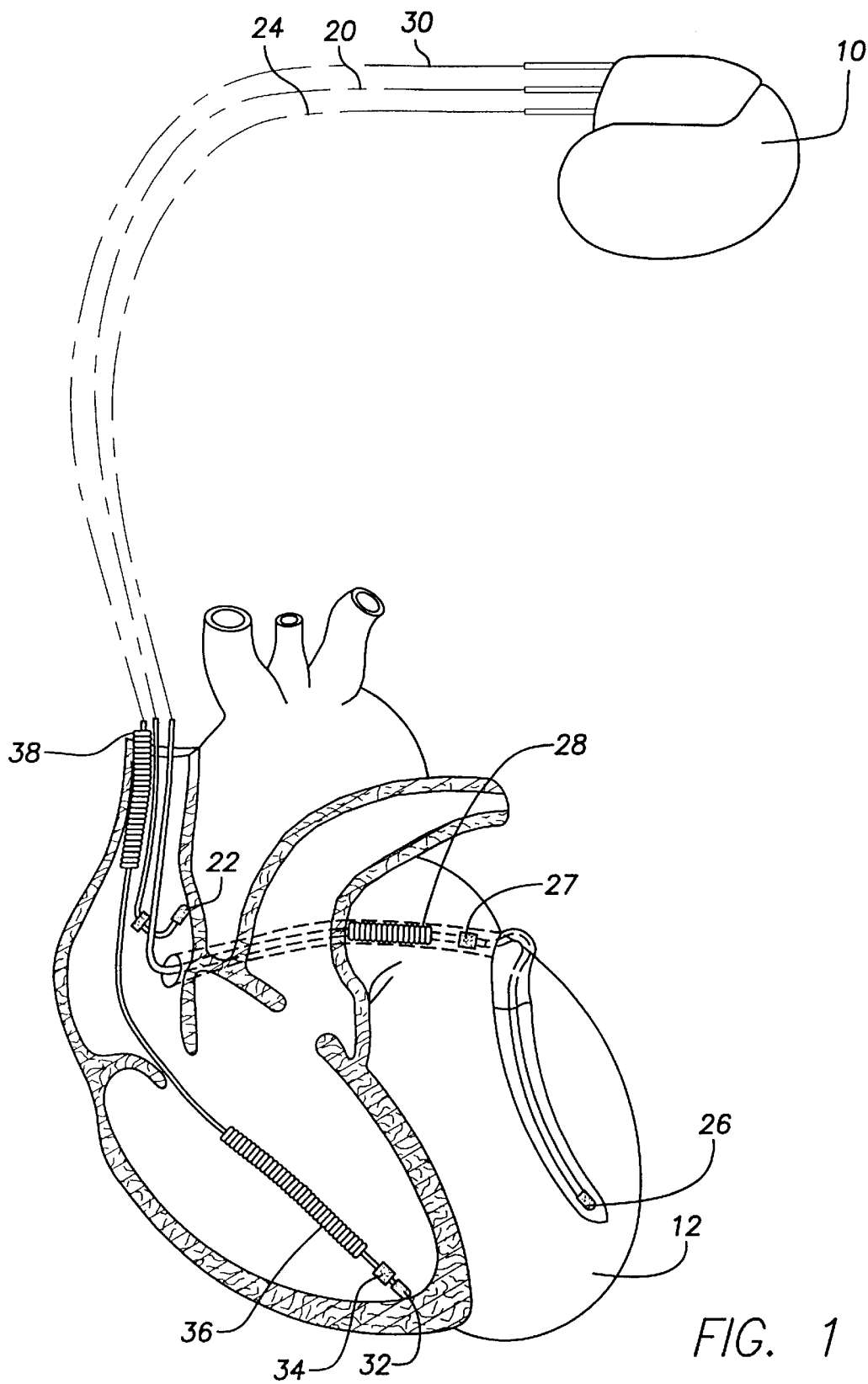
FIG. 1 is a simplified diagram illustrating an implantable stimulation device embodying the present invention in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
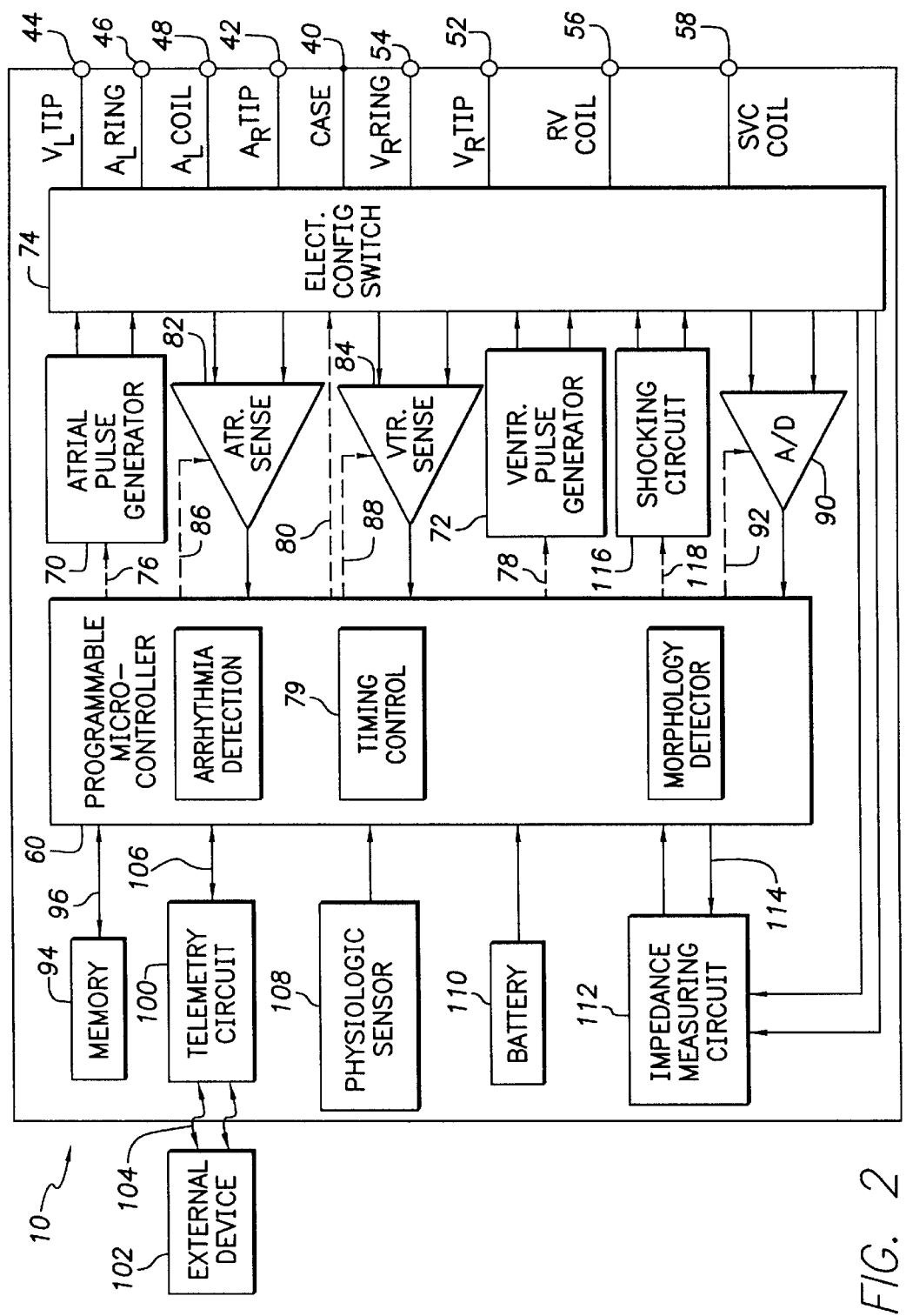
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60, which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art. In accordance with the present invention the timing control 79 also times various time periods such as the extended time period (for example 24 weeks) during which all of the measurements are recorded, time periods (for example 1 week) during which selected histogram values are stored, time intervals (for example 24 hours) when selected measurements are stored, and periodic intervals (for example 30 seconds) when selected measurements are updated. The specific measurements updated, determined, or recorded at these times will be described in detail in connection with the flow charts of FIGS. 4–8.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. In accordance with the present invention, the memory 94 is used to store the activity and respiration measurements and the histogram values over a predetermined extended time period of, for example, 24 weeks, to provide a means by which the progression or regression of heart disease such as congestive heart failure may be monitored.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

The telemetry circuit 100, in accordance with the present invention, may be advantageously employed for transmitting the activity measurements, respiration measurements, and histogram values stored during the predetermined extended period of time in memory 94 to the external programmer 102 for display. Upon display, the progression or regression of the patient's heart disease may be readily observed.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter, which corresponds to the exercise state of the patient.

In accordance with the present invention, the physiologic sensor is used to generate raw activity signals, which are used to derive activity measurements and to determine the activity state of the patient. One such activity measurement is activity variance. For a complete description of a manner in which the activity variance may be determined, reference may be made to U.S. Pat. No. 5,476,483 (Bornzin et al.), issued Dec. 19, 1995, and U.S. Pat. No. 5,514,162 (Bornzin et al.) issued May 7, 1996, which patents are hereby incorporated herein by reference.

The stimulation device additionally includes a battery 110, which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected. Accordingly, the device 10 preferably employs lithium/silver vanadium oxide batteries, as is true for most (if not all) current devices.

As further shown in FIG. 2, the device 10 is shown as having an impedance measuring circuit 112 which is enabled by the microcontroller 60 via a control signal 114. The known uses for an impedance measuring circuit 112 include, but are not limited to, lead impedance surveillance during the acute and chronic phases for proper lead positioning or dislodgment; detecting operable electrodes and automatically switching to an operable pair, if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

The impedance measuring circuit 112, in accordance with particular aspects of the present invention, generates raw sensor signals indicative of the patient's respiration level. An impedance measurement is taken by the impedance measuring circuit 112 applying a current to the lead 30, causing current to flow through the lead toward tip electrode 32 of the lead 30. The measuring current, which is applied to the electrode, preferably has frequency characteristics in the range from about 10 kHz to about 1000 MHz. At these measuring current frequencies, the lead acts as an antenna, which creates a displacement current in the body. The impedance measuring circuit 112 may generate this measuring current in the form of continuous wave current, short-duration pulses of current, or timed pulses of continuous wave current. The impedance measuring circuit 112 measures spatial impedance by determining the potential between the device case 40 and the device connector terminal 44. In this configuration, the device case serves as a reference potential for the device circuitry. Preferably, impedance measuring circuit 112 derives samples at a rate of about 20 per second and communicates these samples to the processor 60. An impedance measuring circuit, which may be utilized in practicing the present invention, is fully described in U.S. Pat. No. 5,201,808 (Steinhaus et al.) issued Apr. 13, 1993, which is incorporated in its entirety herein by reference.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
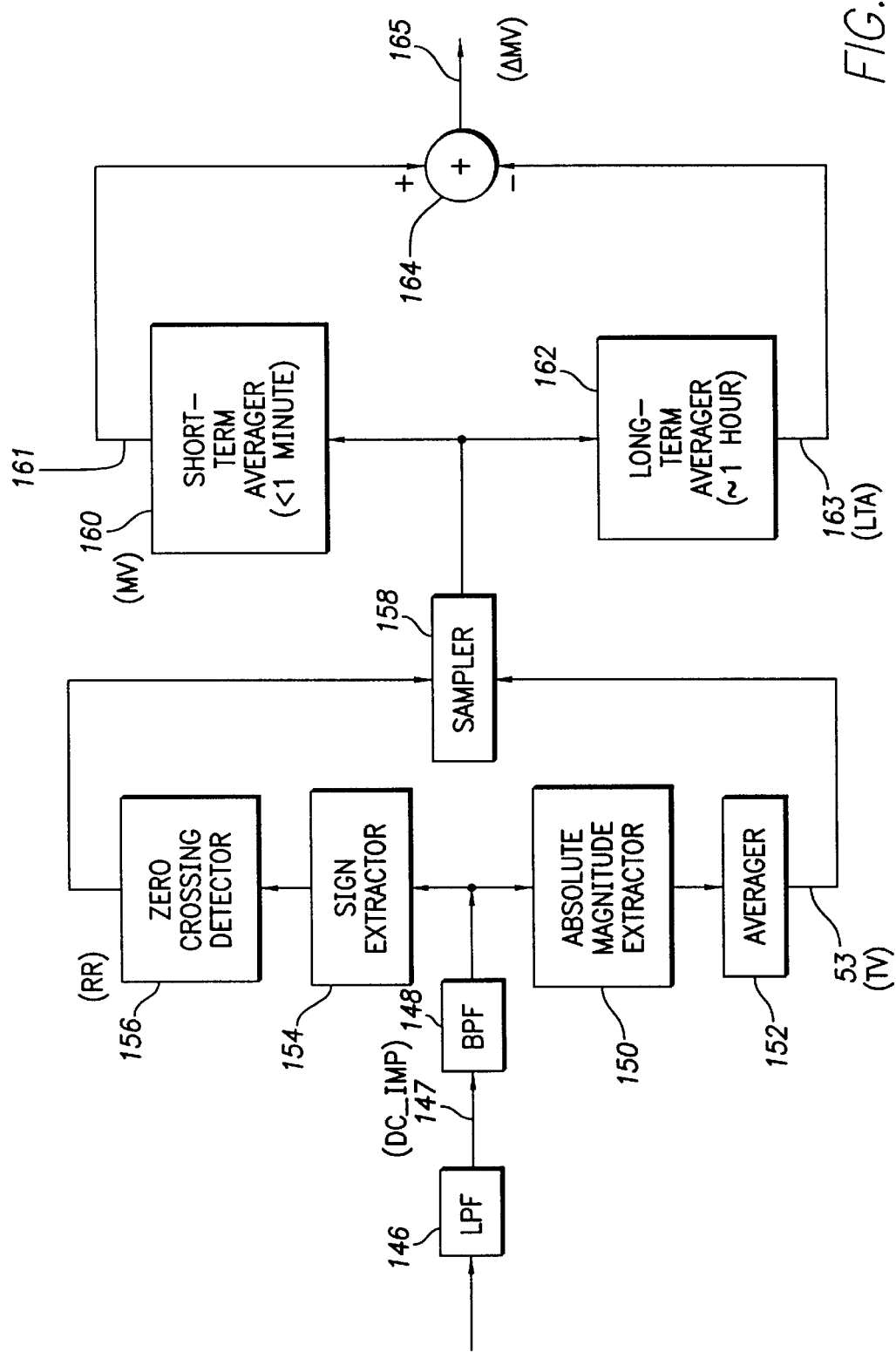
FIG. 3 shows equivalent circuit blocks implemented by a processor which operates on raw respiration sensor signals to determine respiration measurements in accordance with the present invention.

Referring now to FIG. 3, it illustrates the manner in which the processor 60 acts upon the raw respiration signals provided by the impedance measuring circuit 112 in FIG. 2. The impedance measuring circuit 112 derives spatial impedance samples, in the form of signed digital number, at a rate of 20 measurements or higher per second and communicates the samples to a low-pass filter 146. The impedance signals include noise components, cardiac components, and respiration components. The low-pass filter, which preferably has a 1 Hz bandwidth, eliminates the noise and cardiac components from the raw respiration signals. The output 147 of the low-pass filter 146, as a result, represents DC impedance.

The output 147 of the low pass filter 146 is coupled to a bandpass filter 148, which removes the DC impedance offset. The output of the bandpass filter 148, as a result, provides digital samples representing impedance values, which vary about at a level of zero. Negative digital samples indicate that the analog respiration signal is decreasing while positive digital signals signify an increasing signal.

The digital samples are applied to an absolute magnitude extractor 150, which derives the absolute magnitude of each digital sample. The average value of the digital samples is zero because the filter 148 has a gain of zero for DC input. By eliminating the sign from all samples, an averager 152 derives a running average of the absolute magnitudes of the samples. The output 153 of the averager provides the respiration measurement of title volume (TV). Title volume is the measure of the volume of air, which is inhaled or exhaled from the lungs during each breath. It is one parameter, which, as will be seen hereinafter, is stored in the memory 94 during the predetermined extended time period.

The digital samples are also applied to a sign extractor 154, which monitors only the signs, and not the magnitudes, of the digital samples to provide for zero crossing detection. The sign extractor 154 delivers successive bits, each of which represents the sign of a digital sample, to a zero crossing detector 156. The zero crossing detector 156 monitors respiration rate (RR) by ascertaining the timing of changes in the polarity of the impedance measurement signal. Generally, a zero crossing occurs whenever the sign of a digital sample differs from the immediately preceding digital sample. However, there are physiological limits to respiration rate and, therefore, to the frequency of zero crossing. Zero crossings occurring at a rate higher than a predetermined physiological limit must indicate the presence of a noisy respiration signal. Thus, the zero crossing detector analyzes the signs of a number (for example 10) of the most recently acquired samples and determines whether a defined preponderance of samples (for example 7 of 10) have a particular sign. If so, and if the last zero crossing operation, which found a preponderance of a particular sign determined that the majority had an opposite sign, the zero crossing detector 156 presumes the occurrence of a zero crossing. When the sign changes, the zero crossing detector 156 triggers a sampler 158 to read the average value represented by the current value presented by the averager 152. The sampler 158 delivers this average value to both a short-term averager 160 and a long-term averager 162. The short-term averager 160 has a time constant of slightly less than a minute, for example, and the long-term averager 162 has a time constant of about 1 hour, for example.

The output 161 of the short-term averager provides a measure of the instantaneous minute ventilation (MV) or volume and the output 163 of the long-term averager provides a measure of the long-term average (LTA) of minute ventilation.

Because the long-term and sort-term averagers update and accumulate samples at each zero crossing event, the long-term and short-term minute volume values reflect the rate of breathing, as well as the depth of breathing. As will be seen hereinafter, the long-term average or minute volume (LTA) is another parameter, which is stored in the memory 94 during the predetermined extended time period.

As further shown in FIG. 3, a summer 164 derives a delta minute ventilation or volume ($\Delta MV$) measurement which is the difference between the short-term average and long-term average minute volume signals. When the short-term average increases relative to the long-term average causing an increase in $\Delta MV$, this represents an increase in metabolic demand. Conversely, when $\Delta MV$ decreases, there is a decrease in metabolic demand. As will be seen hereinafter, $\Delta MV$ is a parameter which is maintained by the processor in a histogram from which histogram values are derived at time periods of, for example, each week, during the extended time period.

Figure 4:
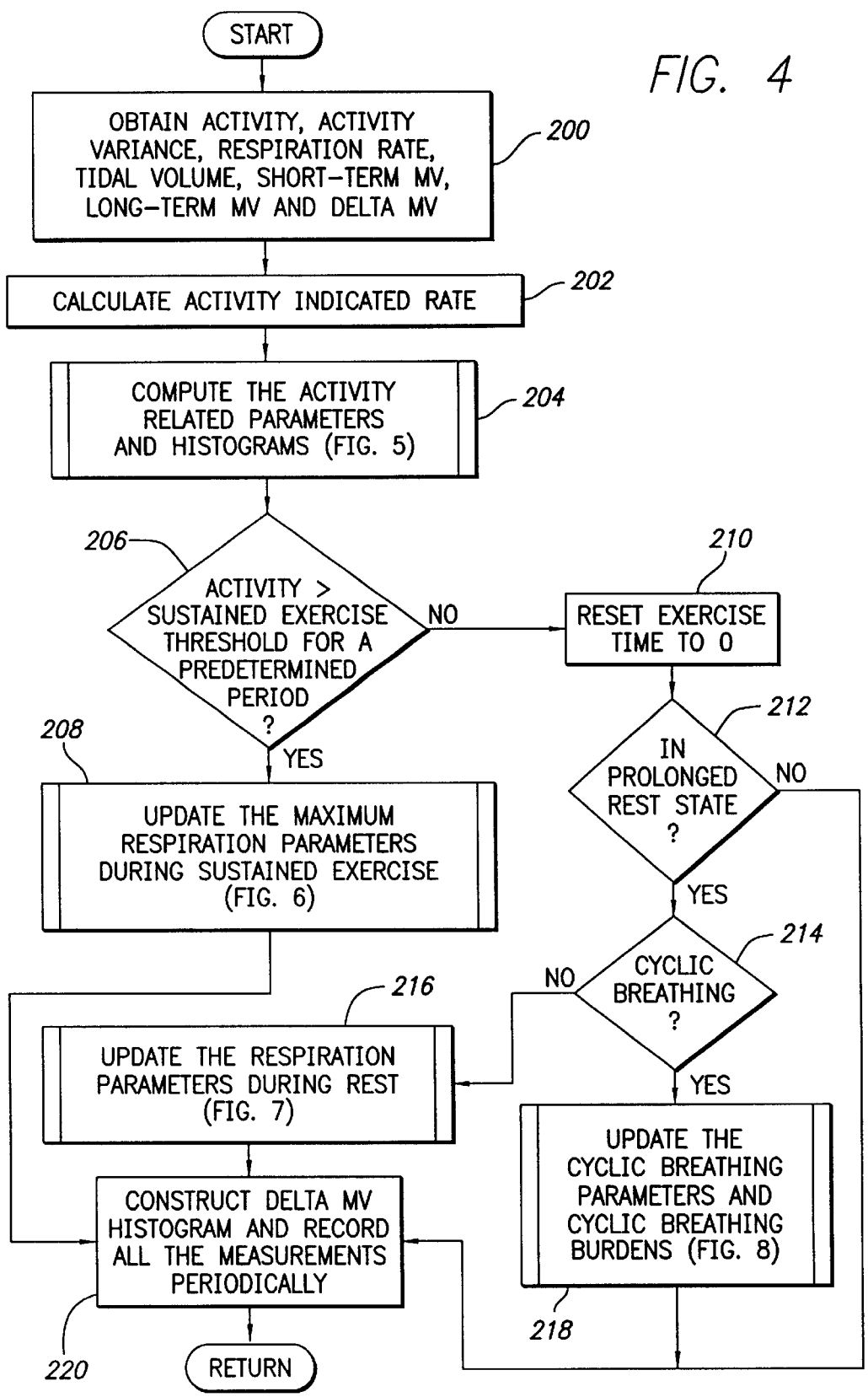
FIG. 4 is a top-level flow chart describing an overview of the operation of one embodiment of the present invention.

FIG. 4 shows a top-level flow chart describing an overview of the operation of the present invention in accordance with a preferred embodiment. The process steps, including those appropriate process steps contained within various sub-routines illustrated in FIG. 4, are performed during each cardiac cycle or alternatively, periodically as, for example, each second.

The process begins with activity block 200 wherein activity and activity variance measurements are determined along with respiration measurements including respiration rate, title volume, short-term minute ventilation, long-term minute ventilation, and delta MV. The activity and activity variance measurements may be determined as described in the referenced Bornzin et al. U.S. Pat. Nos. 5,476,483 and 5,814,162. The respiration measurements are preferably taken as previously described herein with reference to FIG. 3.

Upon completion of activity block 200, the process proceeds to activity block 202. Here, an activity indicated rate (AIR) is determined. A manner in which the AIR may be determined is fully described in the referenced Bornzin et al. U.S. Pat. Nos. 5,476,483 and 5,514,162.

Upon completion of activity block 202, the process advances to sub-routine 204. During sub-routine 204, activity related parameters are computed, and at appropriate intervals, activity parameters are updated, added to the activity histograms, or taken from the histograms and separately stored in memory 94. The sub-routine 204 will be described in detail subsequently with reference to the flow chart of FIG. 5.

After sub-routine 204 is completed, the process advances to decision block 206. Here it is determined if the activity measurement determined in activity block 200 continues to indicate that the patient has been in sustained exercise. More specifically, it is determined in decision block 206 if the activity measurement continues to be greater than an exercise threshold and has been so greater for a period longer than, for example, one minute. The exercise threshold is preferably taken from the activity histogram and represents the activity level corresponding to the histogram value of Activity_70%.

If the result of decision block 206 is affirmative, the process advances to sub-routine 208. In sub-routine 208, the maximum respiration measurements during sustained exercise are updated. The sub-routine 208 will be described subsequently with reference to the flow chart of FIG. 6.

If the result of decision block 206 is negative, the process advances to activity block 210. One measurement associated with sustained exercise of the patient is the time duration of each sustained exercise episode. This time is kept by the timing control 79. If the patient is no longer in an exercise state, the sustained exercise episode duration timer is reset. Here, the sustained exercise episode duration timer will have a value of less than one minute and will be reset in activity block 210 since the patient has not been in an exercise state for a period longer than one minute. The process then advances to decision block 212.

In decision block 212 it is determined if the patient has been in a prolonged rest state. In addition to the activity histogram, a histogram is also maintained for activity variance. A patient is determined to be in prolonged rest, in accordance with decision block 212, if the current activity measurement determined in activity block 200 is less than a prolonged rest threshold. The prolonged rest threshold may be, for example, a long-term average of the activity measurements determined in activity block 200. Such a long-term average is described in the previously referenced Bornzin et al. patents and is referred to therein as STHR. Another condition for an affirmative determination in decision block 212 is that the current activity variance determined in activity block 200 be less than an activity variance threshold. The activity variance threshold may be taken from the activity variance histogram and be the value corresponding to, for example, the histogram value of Act Var_29%.

If it is determined in decision block 212 that the patient is in a prolonged rest state, the process advances to decision block 214 to determine if the patient is in cyclic breathing or normal breathing while in the prolonged rest state. The decision to be made in decision block 214 is preferably based on comparing the current delta MV to a delta MV value obtained from a further histogram. For example, if the current delta MV determined in activity block 200 is greater than a delta MV value corresponding to histogram value MV_60%, for example, the patient may be considered to be in cyclic or periodic breathing. Otherwise, the patient is considered to be in normal breathing during the prolonged rest.

If it is determined in decision block 214 that the patient is in normal breathing while in a prolonged rest, the process advances to sub-routine 216. In sub-routine 216 the respiration parameters for normal breathing are updated. The sub-routine 216 will be described subsequently with respect to the flow chart of FIG. 7. If it is determined in decision block 214 however that the patient is in cyclic breathing, the process proceeds to sub-routine 218. In sub-routine 218 the parametric measurements associated with cyclic breathing along with cyclic breathing burdens are updated. Sub-routine 218 will be described subsequently with reference to FIG. 8.

Lastly, after the sub-routine 218, or after sub-routine 208, or after a negative result in decision block 212 the process advances to activity block 220. In activity block 220 a new delta MV value is loaded into the delta MV histogram if it is time to do so and all other measurements are recorded if it is time to do so. Following activity block 220, the process returns.

Figure 5:
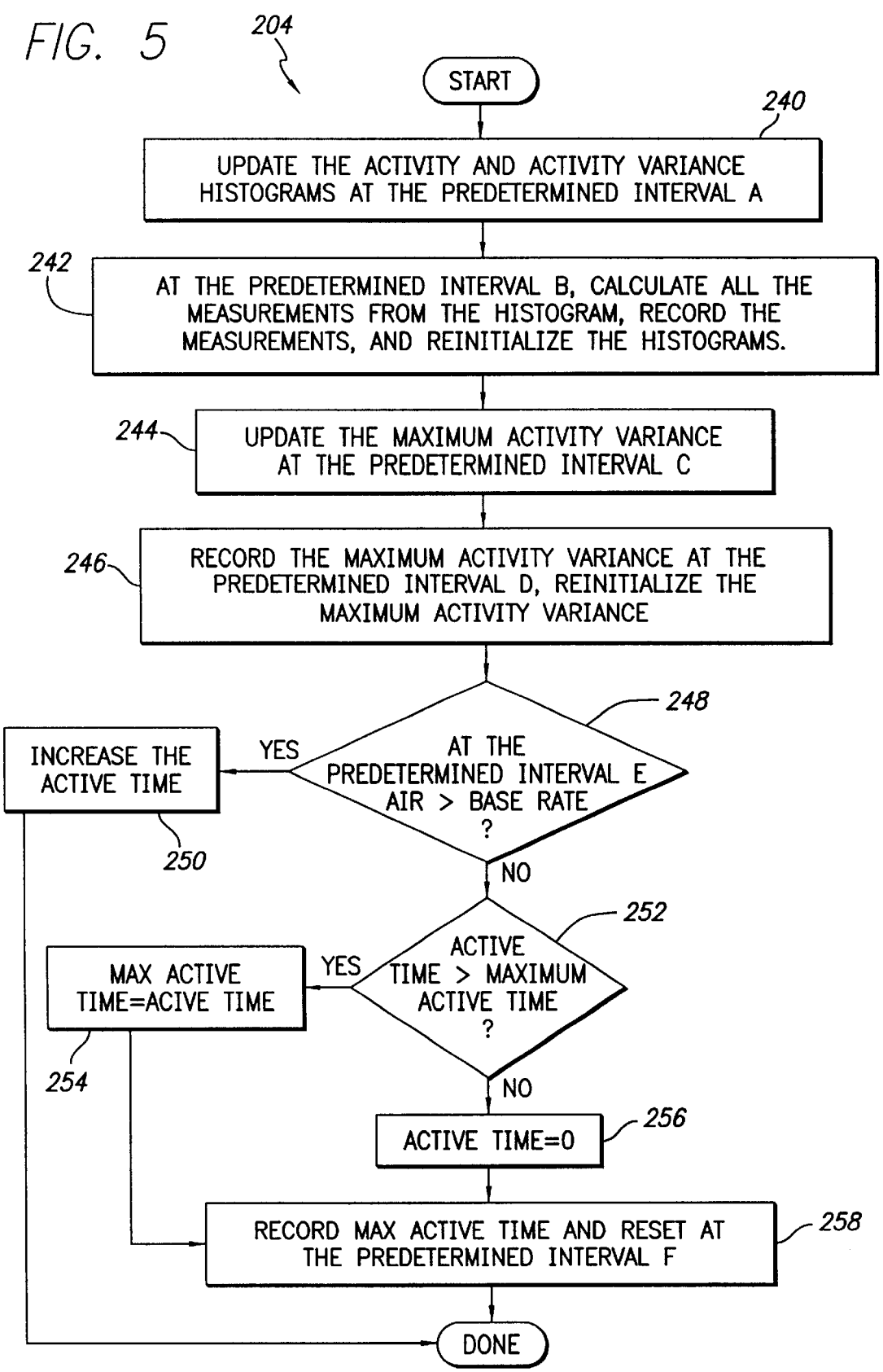
FIG. 5 is a flow chart describing the sub-routine of FIG. 4 for computing the activity related parameters and histograms.

Referring now to FIG. 5, it is a flow chart describing the sub-routine 204 of FIG. 4. The sub-routine initiates at an activity block 240. In accordance with the present invention, the activity and activity variance histograms are updated at periodic intervals, as, for example, every 30 seconds. If it is time to update or add values to the activity and activity variance histograms, this is performed in accordance with activity block 240. Once this is completed or if it is not time to update the activity and activity variance histograms, the process advances to activity block 242. In accordance with activity block 242, at predetermined intervals such as, for example, each week, various measurements are read from the histograms and recorded. In accordance with the present invention, four different histograms are maintained. These histograms include a long-term activity histogram, an activity histogram, an activity variance histogram, and a delta minute ventilation histogram. Each week, from these histograms in accordance with activity block 242, various histogram values are taken from the histograms. These histogram values include activity 99% representing maximal activity, the activity variance histogram bin with the most distribution representing a mode activity variance, and the activity variance_50% value representing a median activity variance. In addition, values for activity variance histogram values of activity variance_16.5%, activity variance_35%, and activity variance_67.5% are also taken. From the delta minute ventilation histogram, values are taken for delta minute ventilation histogram values_12.5%, 85%, 90%, and 95%. The values taken are stored in the memory 94 and the histograms are then cleared.

Once activity block 242 is completed, the process then proceeds to activity block 244. Also in accordance with the present invention, the maximum activity variance value is updated at predetermined intervals of, for example, every 30 seconds. Hence, if it is time to update the maximum activity variance value, activity block 244 is implemented by comparing the current activity variance measurement taken in activity block 200 of FIG. 4 and comparing it to a maximum activity variance value. If the current activity variance value is greater than the maximum activity variance value, the maximum activity variance value is set to be equal to the current activity variance value. Once the maximum activity variance value has been updated or if it is not time to update the maximum activity variance value, the process proceeds to activity block 246. Also in accordance with the present invention, at predetermined time intervals, such as every 24 hours, the maximum activity variance is stored and then the maximum activity variance is reinitialized. Hence, a maximum activity variance is stored each day over a 24-week period. Once the maximum activity variance value is recorded and the maximum activity variance is reinitialized or if it is not time to record the maximum activity variance value, the process advances to decision block 248.

At predetermined intervals such as, every two seconds, it is determined if the patient is in an exercise state. This is performed in accordance with decision block 248 by determining if the activity indicated rate as determined in activity block 202 of FIG. 4 is greater than a base rate. If it is, the process proceeds to activity block 250 to increase an activity timer of timing control 79. Following activity block 250, the sub-routine completes.

If, in accordance with activity block 248, the activity indicated rate is not greater than the base rate, the process proceeds to decision block 252. Here it is determined if the exercise episode time is greater than a maximum exercise time. During the course of a day, a patient may have more than one exercise episode. In accordance with the present invention, it is desired to record each day the duration of the maximum duration exercise episode. As a result, decision block 252 determines if the exercise episode just completed is greater in duration than any other exercise episode which has taken place within the associated 24 hour period. If there is an affirmative determination in decision block 252, the maximum exercise episode duration is set to the current exercise episode duration in activity block 254. If the current exercise episode duration is not greater than a previous maximum exercise episode duration, the process then proceeds to an activity block 256 wherein the exercise episode timer is set to zero. Following either activity block 254 or activity block 256 the process advances to activity block 258 wherein the maximum exercise duration time is stored and the maximum exercise episode duration is reset. This is preferably performed at time intervals of, for example, every 24 hours.

Figure 6:
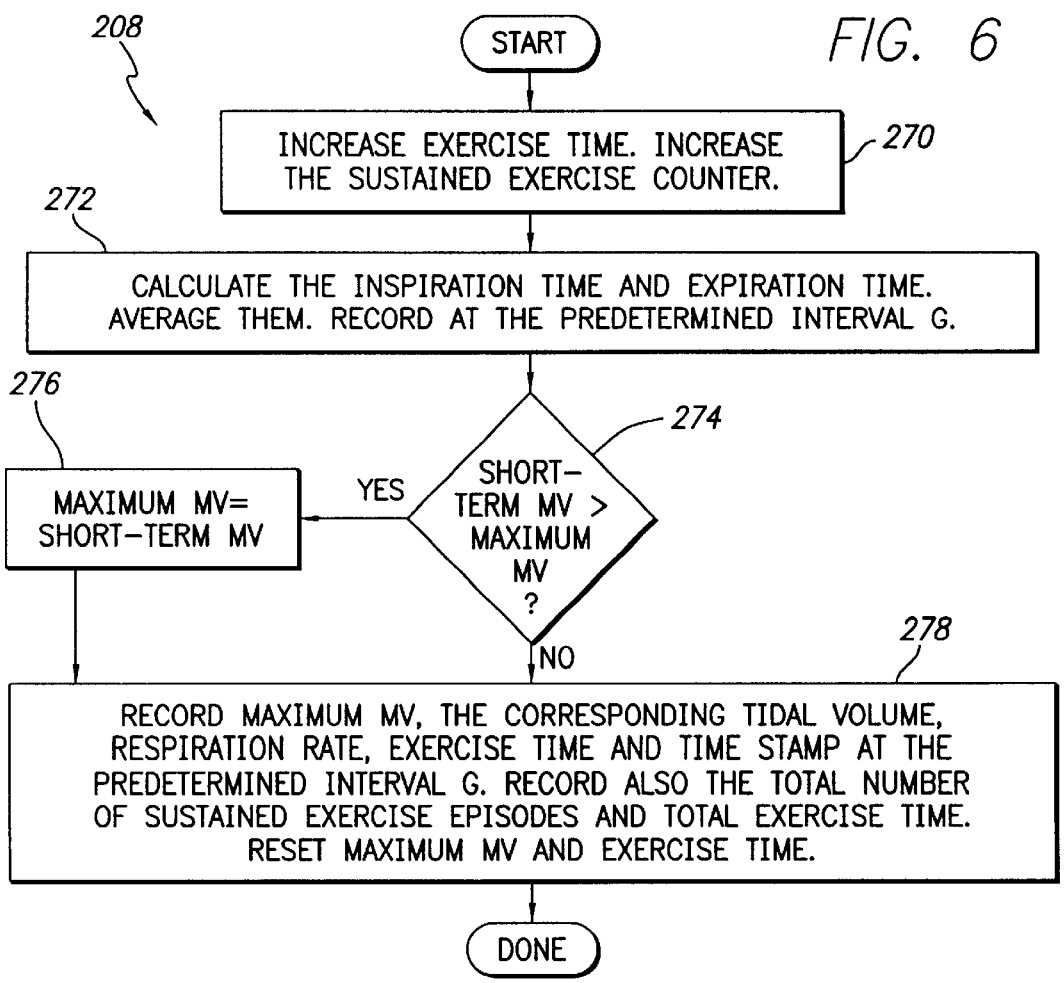
FIG. 6 is a flow chart describing the sub-routine of FIG. 4 for updating the maximum respiration parameters during sustained exercise.

Referring now to FIG. 6, it is a flow chart describing the sub-routine 208 of FIG. 4. As previously mentioned, sub-routine 208 is performed if it is determined in decision block 206 that the patient is in a sustained exercise. The sub-routine 208 initiates at an activity block 270. In accordance with activity block 270, the exercise episode timer is incremented every two seconds and the sustained exercise counter is incremented. The process then advances to activity block 272 wherein the inspiration and expiration times are calculated and averaged during the exercise episode. The average inspiration and expiration times are recorded at predetermined time intervals, as for example, each day.

The process then advances to decision block 274 wherein it is determined if the short-term minute ventilation determined in activity block 200 of FIG. 4 is greater than a maximum minute volume occurring during the current exercise episode. If it is, the maximum minute ventilation is set equal to the current short-term minute ventilation in activity block 276. If the short-term minute ventilation is not greater than a maximum minute ventilation for the exercise episode, then, the maximum minute ventilation is recorded along with its corresponding tidal volume, respiration rate, exercise time, and time stamp each day. Also, in accordance with activity block 278, the total number of sustained exercise episodes occurring during the last 24 hours along with the total exercise time is recorded as well. Maximum minute volume and exercise time is then reset.

Figure 7:
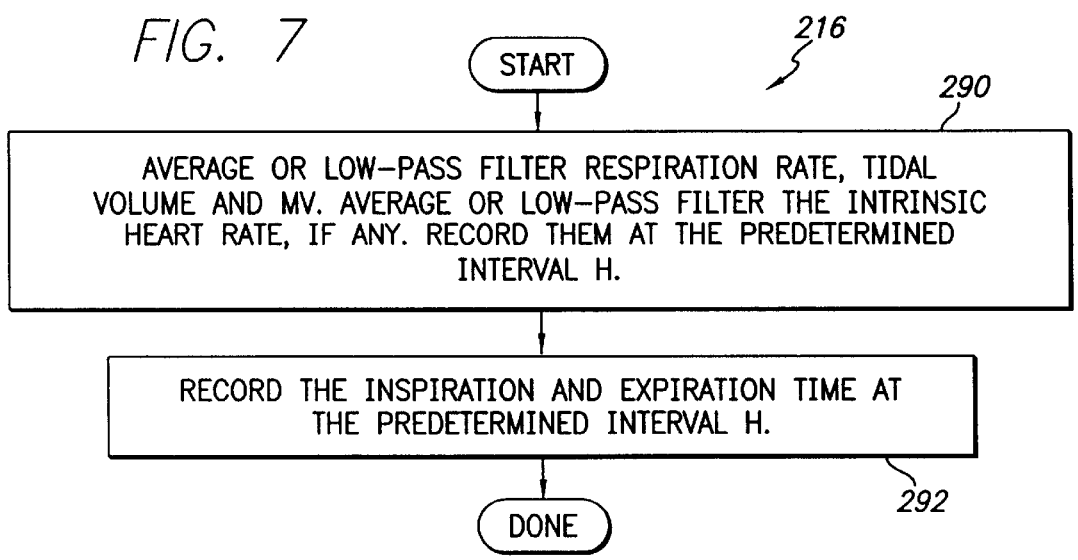
FIG. 7 is a flow chart describing the sub-routine of FIG. 4 for updating the respiration parameters during rest.

Referring now to FIG. 7, it is a flow chart describing the sub-routine 216 of FIG. 4. Sub-routine 216 is performed if, in decision block 214 of FIG. 4, it is determined that the patient is at prolonged rest and is experiencing normal breathing.

The sub-routine 216 initiates at activity block 290. In accordance with the present invention, at predetermined time intervals of, for example, every 24 hours, the tidal volume, respiration rate, and minute ventilation measurements are averaged while the patient is at prolonged rest and experiencing normal breathing. To that end, in accordance with activity block 290, the respiration rate, tidal volume and minute ventilation measurements are averaged or low-pass filtered. In addition, the atrial or intrinsic heart rate is averaged or low-pass filtered as well. Each 24 hours, these values are recorded.

Following activity block 290, the process advances to activity block 292 wherein the inspiration and expiration times are recorded every 24 hours. Following activity block 292, the sub-routine 216 completes.

Figure 8:
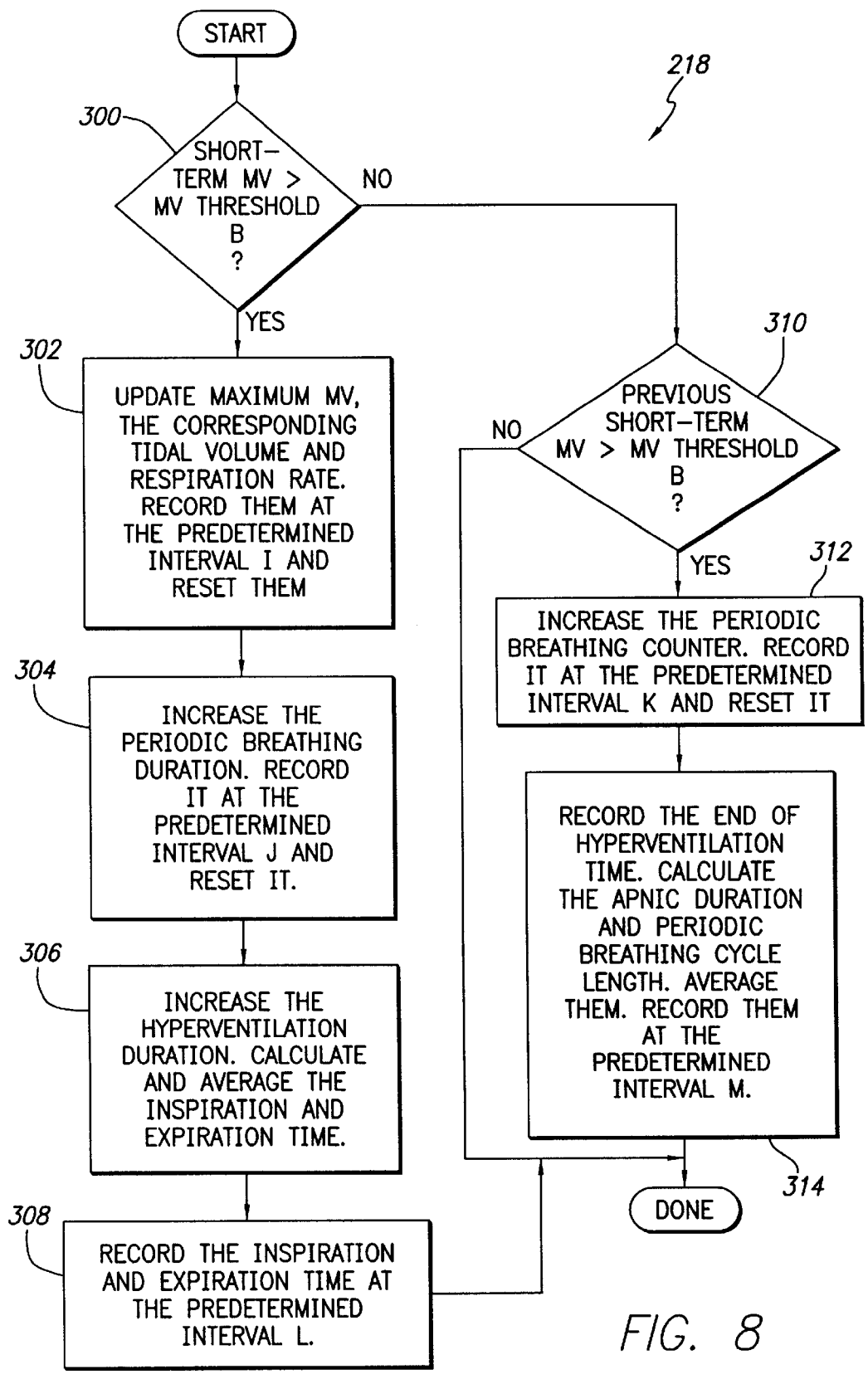
FIG. 8 is a flow chart describing the sub-routine of FIG. 4 for updating the cyclic breathing parameters and cyclic breathing burdens; and, FIG. 9 illustrates an abnormal respiration pattern, more particularly a cyclic breathing pattern, and several respiration parameters, which may be measured and recorded in accordance with the present invention.

Referring now to FIG. 8, it is a flow chart describing the sub-routine 218 of FIG. 4. The sub-routine 218 is performed if, in decision block 214 of FIG. 4, it is determined that the patient is in cyclic breathing during prolonged rest.

Figure 9:
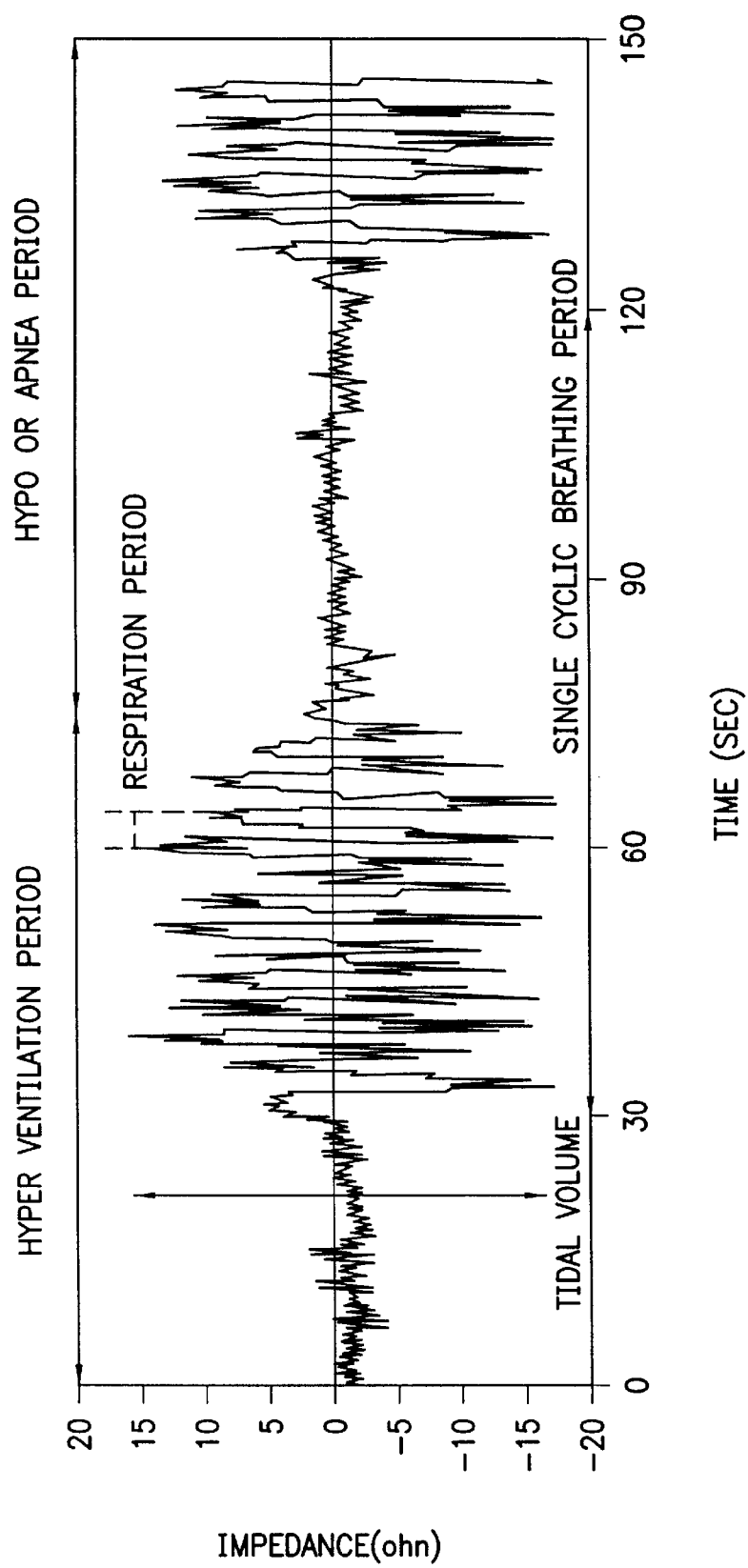

FIG. 9 illustrates a breathing pattern for a patient in cyclic breathing during prolonged rest. As labeled in FIG. 9, the cyclic breathing pattern is characterized by a hyperventilation period and a hypo or apnea period. A single breathing cycle period is defined as extending from the beginning of a hyperventilation period to the beginning of the next hyperventilation period. The hyperventilation period is characterized by large swings in tidal volume and short respiration periods. However, the hypo or apnea period is characterized by essentially no changes in tidal volume. Hence, during the apnic periods, the patient is essentially not breathing.

Referring back to FIG. 8, the sub-routine 218 initiates at a decision block 300 wherein it is determined if the short-term minute ventilation is greater than a predetermined minute ventilation threshold. If the short-term minute ventilation as determined in activity block 200 of FIG. 4 is greater than the threshold, the patient will be considered to be in a hyperventilation period.

The process then advances to activity block 302. In accordance with the present invention, the maximum minute ventilation is updated each day along with its corresponding tidal volume and respiration rate for when the patient is in a hyperventilation period of cyclic breathing. Accordingly, in activity block 302, the maximum minute ventilation and its corresponding tidal volume and respiration rate are recorded each 24 hours and then reinitialized. The process then advances to activity block 304 wherein a periodic breathing duration timer is increased. The periodic breathing duration time is recorded at the end of each predetermined time interval as, for example, every 24 hours and then reset. The process then advances to activity block 306 wherein a hyperventilation duration timer of timing control 79 is increased. Also, the inspiration and expiration times are calculated and averaged. The process then proceeds to activity step 308 wherein the inspiration and expiration average times are recorded at the end of each predetermined time interval as, for example, every 24 hours.

If in decision block 300 it was determined that the short-term minute ventilation is not greater than the minute ventilation threshold, the process then proceeds to decision block 310 where the same determination is repeated. Decision block 310 is performed to determine if the patient is in an apnea period or if the patient is just out of a hyperventilation period. If the result of decision block 310 is negative, the patient is considered to be in an apnea period and the process completes. However, if the result of decision block 310 is in the affirmative, the process proceeds to activity block 312 wherein a periodic breathing counter is incremented. At the end of predetermined time intervals as, for example, every 24 hours, the periodic breathing count is recorded and then reset. The process then advances to activity block 314. At activity block 314 the end of the hyperventilation time is recorded and the apnea period duration and periodic breathing cycle length is calculated. The apnea durations and periodic breathing cycle lengths are then averaged and recorded at predetermined time intervals as, for example, each day.

In addition to providing valuable trend data, the implantable device of the present invention, when in the form of a cardiac rhythm management device of the type illustrated in FIGS. 1 and 2, may itself automatically adjust pacing therapy responsive to the physiological parameter measurements. For example, the processor 60 may be programmed to access the cyclic breathing data to determine if the patient is experiencing troubled breathing. Such troubled breathing is due to an upset in carbon dioxide and oxygen equilibrium in the blood. The processor may be programmed to increase the pacing rate to cause an improvement in the patient's breathing condition. In some patients, only a slight rate increase of 5% to 10% can make a perceived difference in breathing comfort.

Thus, an implantable cardiac device and method for monitoring a progression or regression in heart disease over an extended time period and adapting cardiac rhythm management therapy are provided. When the implanted device transmits the stored parameter measurements to an external device such as an external programmer, the data relating to the progression or regression of the heart disease such as congestive heart failure will be made available to the physician. The physician will have a wealth of information from which the progression or regression of the heart disease may be discerned. In summary, the data available to the physician will include a maximum activity variance taken each day, a maximum active time taken each day, sustained exercise maximum minute ventilation and corresponding exercise duration, respiration rate, tidal volume, and time stamp taken each day, total count of exercise episodes taken each day, and total duration of sustained exercise episodes for each day. In addition, the physician will be provided data indicating the prolonged rest average respiration rate, tidal volume, and minute ventilation and average atrial rate recorded each day. The physician will also be provided with data indicating the maximum minute ventilation and corresponding tidal volume and respiration rate for cyclic hyperventilation periods each day, a periodic breathing count for each day, a periodic breathing duration for each day, and inspiration and expiration average times for each day. The physician will further be provided with averaged apnea duration and periodic breathing cycle times taken each day. All of the foregoing data is taken over a six month period.

In addition to the data above, the doctor will also be provided with histogram values taken each week. These histogram values include activity_99%, mode and median activity variance values, activity variance_16.5%, 35%, and 67.5%, and delta minute ventilation histogram values_ 12.5%, 85%, 90%, and 95%.

While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. An implantable cardiac device that monitors a progression or regression in congestive heart failure of a patient, during an extended time period, comprising:
   an activity sensor that generates raw sensor signals indicative of the patient's activity level, wherein a degradation or improvement of the patient's activity level over time corresponds to an indication of the progression or regression of congestive heart failure;
   a processor coupled to the activity sensor that processes the raw signals to determine activity measurements;
   a memory coupled to the processor that stores the activity measurements during the extended time period; and
   a telemetry circuit that transmits the activity measurements stored during the extended time period to an external monitor for display.

2. The device of claim 1 wherein the processor determines activity variance measurements.

3. The device of claim 1 wherein the extended time period encompasses a plurality of time intervals and wherein the processor stores in the memory a maximum activity variance measurement for each of the time intervals.

4. The device of claim 1 wherein the extended time period encompasses a plurality of time intervals and wherein the processor, periodically during each time interval, determines short-term activity measurements and corresponding long-term activity measurements and, during each time interval, stores in the memory a maximum active time, the maximum active time being a longest continuous time in which short-term activity measurements are greater than their corresponding long-term activity measurements.

5. The device of claim 1 wherein the extended time period encompasses a plurality of time periods and wherein the processor maintains a histogram of the activity measurements made during each time period, determines at least one histogram value for each time period, and stores the histogram values in the memory.

6. The device of claim 5 wherein the at least one histogram value corresponds to a maximum activity.

7. The device of claim 5 wherein the at least one histogram value corresponds to a mode activity variance.

8. The device of claim 5 wherein the at least one histogram value corresponds to a median activity variance.

9. The device of claim 1 further including a heart rate monitor, wherein the extended time period encompasses a plurality of time intervals, and wherein the processor stores in the memory after each time interval an average heart rate of the patient for when the patient is at rest.

10. The device of claim 9 wherein the average heart rate is an average atrial rate.

11. The device of claim 1 wherein the extended time period encompasses a plurality of time intervals and wherein the processor stores in the memory after each time interval a number of exercise episodes of the patient occurring during the time interval.

12. The device of claim 11 wherein each exercise episode is a continuous period of time longer than a preset time in which the activity measurements are above a given threshold.

13. The device of claim 11 wherein the processor further stores in the memory the cumulative time of the exercise episodes.

14. An implantable cardiac device that monitors, during an extended time period, a progression or regression in congestive heart failure of a patient comprising:
  a respiration sensor that generates raw sensor signals indicative of the patient's respiration, wherein a degradation or improvement of the patient's respiration level over time corresponds to an indication of the progression or regression of congestive heart failure;
  a processor coupled to the respiration sensor that processes the raw signals to determine respiration measurements;
  a memory coupled to the processor that stores the respiration measurements during the extended time period; and
  a telemetry circuit that transmits the respiration measurements stored during the extended time period to an external monitor for display.

15. The device of claim 14 wherein the extended time period encompasses a plurality of time intervals and wherein the processor stores in the memory a maximum respiration measurement for each of the time intervals.

16. The device of claim 14 wherein the extended time period encompasses a plurality of time periods and wherein the processor, periodically, during each time period, determines a short-term minute volume measurement, a corresponding long-term minute volume measurement and a delta minute volume measurement based upon the difference between a short-term minute volume measurement and its corresponding long-term minute volume measurement.

17. The device of claim 16 wherein the processor maintains a histogram of the delta minute volume measurements made during each time period, determines at least one histogram value for each time period, and stores the histogram values in the memory.

18. The device of claim 14 wherein the respiration measurements include tidal volume, minute volume, and respiration rate.

19. The device of claim 14 further including an activity sensor that senses activity of the patient and wherein the processor determines the respiration measurements when the patient is in at least one given activity state.

20. The device of claim 19 wherein the processor determines the respiration measurements when the patient is in an exercise state.

21. The device of claim 20 wherein the extended time period encompasses a plurality of time intervals and wherein the processor stores in the memory exercise state respiration measurements for each of the time intervals.

22. The device of claim 21 wherein the respiration measurements include maximum respiration rate, maximum tidal volume, and maximum minute volume.

23. The device of claim 20 wherein the extended time interval encompasses a plurality of time intervals, wherein the processor determines the respirations measurements for each one of patient exercise episodes occurring during each time interval and stores in the memory the respiration measurements corresponding to a given one of the exercise episodes for each time interval.

24. The device of claim 23 wherein the respiration measurements include minute volume, and wherein the given one of the exercise episodes is the exercise episode yielding a greatest maximum minute volume.

25. The device of claim 24 wherein the stored respiration measurements include maximum respiration rate, maximum tidal volume, and maximum minute volume.

26. The device of claim 25 wherein the processor further stores a duration of the given exercise episode and a time stamp of the given exercise episode.

27. The device of claim 19 wherein the processor determines the respiration measurements when the patient is in a prolonged rest state.

28. The device of claim 27 wherein the extended time period encompasses a plurality of time intervals and wherein the processor stores in the memory average prolonged rest state respiration measurements for each time interval.

29. The device of claim 28 wherein the average respiration measurements include tidal volume, respiration rate, and minute volume.

30. The device of claim 29 wherein the processor determines the respiration measurements when the activity sensor and the respiration sensor indicate the patient is at rest and undergoing periodic breathing.

31. The device of claim 30 wherein the extended time period encompasses a plurality of time intervals and wherein the processor stores in the memory maximum respiration measurements for each time interval.

32. The device of claim 31 wherein the respiration measurements include maximum respiration rate, maximum tidal volume, and maximum minute volume.

33. The device of claim 32 wherein the stored maximum respiration rate and maximum tidal volume correspond in time to the maximum minute volume.

34. The device of claim 30 further including a counter and wherein the processor further increments the counter at periodic intervals when the patient is at rest and undergoing periodic breathing.

35. The device of claim 34 wherein the extended time period encompasses a plurality of time intervals and wherein the processor stores in the memory a total count for each time interval.

36. The device of claim 30 further including a timer and wherein the processor further increments the timer at periodic intervals when the patient is at rest and undergoing periodic breathing.

37. The device of claim 36 wherein the extended time period encompasses a plurality of time intervals and wherein the processor stores in the memory a total timer duration for each time interval.

38. The device of claim 19 wherein the processor determines minute volume measurements when the patient is at rest and determines the presence of cycling breathing when the minute volume is less than a given threshold.

39. The device of claim 38 wherein the processor determines at least one respiration of measurement of hyperventilation period, hypoventilation period, single cycle breathing period, cycles per cycling breathing episode and total time of cycling breathing.

40. The device of claim 39 wherein the extended time period encompasses a plurality of time intervals and wherein the processor stores in the memory the at least one respiration measurement for each time interval.

41. An implantable cardiac device that monitors a progression or regression in congestive heart failure of a patient during an extended time period, comprising:
an activity sensor that generates raw sensor signals indicative of the patient's activity level, wherein a degradation or improvement of the patient's activity level over time corresponds to an indication of the progression or regression of congestive heart failure;
a respiration sensor that generates raw sensor signals indicative of the patient's respiration, wherein a degradation or improvement of the patient's respiration level over time corresponds to an indication of the progression or regression of congestive heart failure;
a processor coupled to the activity sensor that processes the raw signals to determine activity and minute volume measurements;
a memory coupled to the processor that stores the activity and minute volume measurements during the extended time period; and
a telemetry circuit that transmits the activity and minute volume measurements stored during the extended time period to an external monitor for display.

42. The device of claim 41 wherein the processor determines delta minute volume measurements based upon the minute volume measurements, creates histograms of the activity and delta minute volume measurements and at spaced apart times derives histogram values from the histograms.

43. The device of claim 42 wherein the processor stores the histogram values in the memory.

44. An implantable cardiac device that provides historical physiological parameter measurements indicative of a progression or regression in congestive heart failure of a patient comprising:
activity sensing means for generating raw sensor signals indicative of the patient's activity level, wherein a degradation or improvement of the patient's activity level over time corresponds to an indication of the progression or regression of congestive heart failure;
processing means for processing the raw signals to determine activity measurements;
storage means for storing the activity measurements during an extended time period; and
telemetry means for transmitting the stored activity measurements to an external monitor for display.

45. The device of claim 44 wherein the processing means includes means for determining activity variance measurements.

46. The device of claim 44 wherein the extended time period encompasses a plurality of time intervals and wherein the processing means includes means for storing in the memory a maximum activity variance measurement for each of the time intervals.

47. The device of claim 44 wherein the extended time period encompasses a plurality of time intervals and wherein the processing means includes means for periodically, during each time interval, determining short-term activity measurements and corresponding long-term activity measurements and, during each time interval, storing in the storage means a maximum active time, the maximum active time being a longest continuous time in which short-term activity measurements are longer than the corresponding long-term activity measurements.

48. The device of claim 44 wherein the extended time period encompasses a plurality of time periods and wherein the processing means includes means for maintaining a histogram of the activity measurements made during each time period, means for determining at least one histogram of the activity measurements made during each time period, means for determining at least one histogram value for each time period, and means for storing the histogram values in the storage means.

49. The device of claim 48 wherein the at least one histogram value corresponds to a maximum activity.

50. The device of claim 48 wherein the at least one histogram value corresponds to a mode activity variance.

51. The device of claim 48 wherein the at least one histogram value corresponds to a median activity variance.

52. The device of claim 44 further including means for monitoring heart rate, wherein the extended time period encompasses a plurality of time intervals, and wherein the processing means includes means for storing in the storage means after each time interval an average heart rate of the patient for when the patient is at rest.

53. The device of claim 52 wherein the average heart rate is an average atrial rate.

54. The device of claim 44 wherein the extended time period encompasses a plurality of time intervals and wherein the processing means includes means for storing in the storage means after each time intervals a number of exercise episodes of the patient occurring during the time interval.

55. The device of claim 54 wherein each exercise episode is a continuous period of time longer than a preset time in which the activity measurements are above a given threshold.

56. The device of claim 54 wherein the processor further includes means for storing in the storage means the cumulative time of the exercise episodes.

57. An implantable cardiac device that provides historical physiological parameter measurements indicative of a progression or regression in congestive heart failure of a patient comprising:
respiration sensing means for generating sensor signals indicative of the patient's respiration, wherein a degradation or improvement of the patient's respiration level over time corresponds to an indication of the progression or regression of congestive heart failure;
processing means for processing the raw signals to determine respiration measurements;
storage means for storing the respiration measurements during an extended time period; and
telemetry means for transmitting the stored respiration measurements to an external monitor for display.

58. The device of claim 57 wherein the extended time period encompasses a plurality of time intervals and wherein the processing means includes means for storing in the storage mans a maximum minute volume measurement for each of the time intervals.

59. The device of claim 57 wherein the extended time period encompasses a plurality of time periods and wherein the processing means includes means for periodically, during each time period, determining a short-term minute volume measurement, a corresponding long-term minute volume measurement, and a delta minute volume measurement based upon the difference between a short-term minute volume measurement and its corresponding long-term minute volume measurement.

60. The device of claim 59 wherein the processing means includes means for maintaining a histogram of the delta minute volume measurements made during each time interval, means for determining at least one histogram value for each time period, and means for storing the histogram values in the storage means.

61. The device of claim 57 wherein the respiration measurements include tidal volume, minute volume and respiration rate.

62. The device of claim 57 further including activity sensing means for sensing activity of the patient and wherein the processing means determines the respiration measurements when the patient is in at least one given activity state.

63. The device of claim 62 wherein the processing means determines the respiration measurements when the patient is in an exercise state.

64. The device of claim 63 wherein the extended time period encompasses a plurality of time intervals and wherein the processing means includes means for storing in the storage means exercise state respiration measurements for each of the time intervals.

65. The device of claim 64 wherein the respiration measurements include maximum respiration rate, maximum tidal volume, and maximum minute volume.

66. The device of claim 63 wherein the extended time interval encompassed a plurality of time intervals, wherein the processing means determines the respirations measurements for each one of patient exercise episodes occurring during each time interval and includes means for storing in the storage means the respiration measurements corresponding to a given one of the exercise episodes for each time interval.

67. The device of claim 66 wherein the respiration measurements include minute volume, and wherein the given one of the exercise episodes is the exercise episode yielding a greatest maximum minute volume.

68. The device of claim 67 wherein the stored respiration measurements include maximum respiration rate, maximum tidal volume, and maximum minute volume.

69. The device of claim 68 wherein the processing means further includes means for storing a duration of the given exercise episode and a time stamp of the given exercise episode.

70. The device of claim 62 wherein the processing means determines the respiration measurements when the patient is in a prolonged rest state.

71. The device of claim 70 wherein the extended time period encompasses a plurality of time intervals and wherein the processing means includes means for storing in the storage means average prolonged rest state respiration measurements for each time interval.

72. The device of claim 71 wherein the average respiration measurements include tidal volume, respiration rate, and minute volume.

73. The device of claim 62 wherein the processing means determines the respiration measurements when the activity sensing means and the respiration sensing means indicate the patient is at rest and undergoing periodic breathing.

74. The device of claim 73 wherein the extended time period encompasses a plurality of time intervals and wherein the processing means includes means for storing in the storage mans maximum respiration measurements for each time interval.

75. The device of claim 74 wherein the respiration measurements include maximum respiration rate, maximum tidal volume, and maximum minute volume.

76. The device of claim 75 wherein the stored maximum respiration rate and maximum tidal volume correspond in time to the maximum minute volume.

77. The device of claim 73 further including means for counting and wherein the processing means further includes means for incrementing the means for counting at periodic intervals when the patient is at rest and undergoing periodic breathing.

78. The device of claim 77 wherein the extended time period encompasses a plurality of time intervals and wherein the processing means includes means for storing in the storage means a total count for each time interval.

79. The device of claim 73 further including means for timing and wherein the processor further includes means for incrementing the means for timing at periodic intervals when the patient is at rest and undergoing periodic breathing.

80. The device of claim 79 wherein the extended time period encompasses a plurality of time intervals and wherein the processing means includes means for storing in the storage means a total duration of the means for timing for each time interval.

81. The device of claim 62 wherein the processing means includes means for determining minute volume measurements when the patient is at rest and the presence of cycling breathing when the minute volume is less than a given threshold.

82. The device of claim 81 wherein the processing means determines at least one respiration of measurement of hyperventilation period, hypoventilation period, single cycle breathing period, cycles per cycling breathing episode and total time of cycling breathing.

83. The device of claim 82 wherein the extended time period encompasses a plurality of time intervals and wherein the processing means includes means for storing in the storage means the at least respiration measurement for each time interval.

84. An implantable cardiac device that provides historical physiological parameter measurements indicative of a progression or regression in congestive heart failure condition of a patient comprising:
   activity sensing means for generating raw sensor signals indicative of the patient's activity level, wherein a degradation or improvement of the patient's activity level over time corresponds to an indication of the progression or regression of congestive heart failure;
   respiratory sensing means for generating raw sensor signals indicative of the patient's respiration, wherein a degradation or improvement of the patient's respiration level over time corresponds to an indication of the progression or regression of congestive heart failure;
   processing means for processing the raw signals to determine activity and respiration volume measurements;
   storage means for storing the activity and respiration measurements during an extended time period; and telemetry means for transmitting the stored activity and respiration measurements to an external monitor for display.

85. The device of claim 84 wherein the processing means includes means for determining delta minute volume measurements based upon the minute volume measurements, means for creating histograms of the activity and delta minute volume measurements, and means for deriving histogram values from the histogram at spaced apart times.

86. The device of claim 84 wherein the processing means includes means for storing the histogram values in the storage means.

87. In an implantable cardiac device, a method of providing historical physiological parameter measurements indicative of a progression or regression in a patient's congestive heart failure condition, the method including the steps of:
generating raw signals indicative of the patient's activity level, wherein a degradation or improvement of the patient's activity level over time corresponds to an indication of the progression or regression of congestive heart failure;
processing the raw signals to determine activity measurements;
storing the activity measurements during an extended time period; and
transmitting the stored activity measurements to an external monitor for display.

88. The method of claim 87 wherein the processing step includes determining activity variance measurements.

89. The method of claim 87 wherein the extended time period encompasses a plurality of time intervals and wherein the processing step includes determining a maximum activity variance measurement for each of the time intervals.

90. The method of claim 87 wherein the time period encompasses a plurality of time intervals and wherein the processing step includes periodically, during each time interval, determining short-term activity measurements and corresponding long-term activity measurements and, during each time interval, storing in the memory a maximum active time, the maximum active time being a longest continuous time in which short-term activity measurements are greater than the corresponding long-term activity measurements.

91. The method of claim 87 wherein the extended time period encompasses a plurality of time periods and wherein the processing step includes maintaining a histogram of the activity measurements made during each time period and determining at least one histogram value for each time period.

92. The method of claim 91 wherein the at least one histogram value corresponds to maximum activity of the patient.

93. The method of claim 91 wherein the maintaining step includes the step of maintaining a histogram of activity variance measurements.

94. The method of claim 93 wherein the determining step includes determining a histogram value corresponding to mode activity variance.

95. The method of claim 93 wherein the determining step includes determining a histogram value corresponding to median activity variance.

96. The method of claim 87 wherein the extended time period encompasses a plurality of time intervals and wherein the method further includes the steps of monitoring heart rate of the patient and storing, for each time interval, an average heart rate of the patient for when the patient is at rest.

97. The method of claim 96 wherein the average heart rate is an average atrial rate.

98. The method of claim 87 wherein the extended time period encompasses a plurality of time intervals and method further includes the steps of determining exercise episodes of the patient and storing, for each time interval, a number of exercise episodes of the patient.

99. The method of claim 98 including the further step of counting an exercise episode when a continuous period of time longer than a preset time elapses in which the activity measurements are above a given threshold.

100. The method of claim 98 including the further step of storing a cumulative time of the exercise episodes.

101. In an implantable cardiac device, a method of providing historical physiological parameter measurements indicative of a progression or regression in a patient's congestive heart failure, the method including the steps of:
generating raw signals indicative of the patient's respiration, wherein a degradation or improvement of the patient's respiration level over time corresponds to an indication of the progression or regression of congestive heart failure;
processing the raw signals to determine respiration measurements;
storing the respiration measurements during an extended time period; and
transmitting the stored respiration measurements to an external monitor for display.

102. The method of claim 101 wherein the extended time period encompasses a plurality of time intervals and wherein the processing step includes determining a maximum minute volume measurement for each of the time intervals.

103. The method of claim 101 wherein the extended time period encompasses a plurality of time periods and wherein the processing step includes periodically, during each time period, determining a short-term minute volume measurement, a corresponding long-term minute volume measurement, and a delta minute volume measurement based upon the difference between a short-term minute volume measurement and its corresponding long-term minute volume measurement.

104. The method of claim 103 wherein the processing step includes maintaining a histogram of the delta minute volume measurements made during each time period and determining at least one histogram value for each time period.

105. The method of claim 101 wherein the respiration measurements include tidal volume, minute volume and respiration rate.

106. The method of claim 101 further including the step of sensing activity of the patient and wherein the respiration measurements are determined when the patient is in at least one given activity state.

107. The method of claim 106 wherein the respiration measurements are determined when the patient is in an exercise state.

108. The method of claim 107 wherein the extended time period encompasses a plurality of time intervals and wherein the storing step includes storing the respiration measurements for each of the time intervals.

109. The method of claim 108 wherein the respiration measurements include maximum respiration rate, maximum tidal volume, and maximum minute volume.

110. The method of claim 107 wherein the extended time period encompasses a plurality of time intervals and wherein the method further includes the steps of determining exercise episodes of the patient, determining the respiration measurements for each exercise episode, and storing the respiration measurements corresponding to a given one of the exercise episodes for each time interval.

111. The method of claim 110 wherein the respiration measurements include minute volume, and wherein the given one of the exercise episodes is the exercise episode yielding a greatest maximum minute volume.

112. The method of claim 111 wherein the stored respiration measurements include maximum respiration rate, maximum tidal volume, and maximum minute volume.

113. The method of claim 112 including the further step of storing duration of the given exercise episode and a time stamp corresponding to the given exercise episode.

114. The method of claim 106 including the further step of determining prolonged rest states of the patient and wherein the respiration measurements are determined when the patient is in a prolonged rest state.

115. The method of claim 114 wherein the extended time period encompasses a plurality of time intervals and wherein the storing step includes storing average prolonged rest state respiration measurements for each time interval.

116. The method of claim 115 wherein the averaged respiration measurements include tidal volume, respiration rate, and minute volume.

117. The method of claim 106 including the further step of determining when the patient is at rest and undergoing periodic breathing.

118. The method of claim 117 wherein the extended time period encompasses a plurality of time intervals and wherein the method further includes the step of storing maximum respiration measurements for each time interval for when the patient is at rest and undergoing periodic breathing.

119. The method of claim 118 wherein the respiration measurements include maximum respiration rate, maximum tidal volume, and maximum minute volume.

120. The method of claim 119 wherein the stored maximum respiration rate and maximum tidal volume correspond in time to the maximum minute volume.

121. The method of claim 117 including the further step of counting at periodic intervals when the patient is at rest and undergoing periodic breathing.

122. The method of claim 121 wherein the extended time period encompasses a plurality of time intervals and wherein the method includes the further steps of providing and storing a total count for each time interval.

123. The method of claim 117 including the further step of timing when the patient is at rest and undergoing periodic breathing.

124. The method of claim 123 wherein the extended time period encompasses a plurality of time intervals and wherein the method further includes the steps of providing and storing a total time duration for each time interval for when the patient is at rest and undergoing periodic breathing.

125. The device of claim 106 including the further steps of determining minute volume measurements when the patient is at rest and determining the presence of cycling breathing when the minute volume is less than a given threshold.

126. The method of claim 125 wherein the processing step includes determining at least one respiration of measurement of hyperventilation period, hypoventilation period, single cycle breathing period, cycles per cycling breathing episode and total time of cycling breathing.

127. The method of claim 126 wherein the extended time period encompasses a plurality of time intervals and wherein the storing step includes storing the at least one respiration measurement for each time interval.

128. In an implantable cardiac device a method of providing historical physiological parameter measurements indicative of progression or regression in a patient's congestive heart failure condition including the steps of:

generating raw signals indicative of the patient's activity level, wherein a degradation of the patient's activity level over time corresponds to an indication of the progression or regression of congestive heart failure;

generating raw signals indicative of the patient's respiration, wherein a degradation or improvement of the patient's respiration level over time corresponds to an indication of the progression or regression of congestive heart failure;

processing the raw signals to determine activity and respiration measurements;

storing the activity and respiration measurements during an extended time period; and transmitting the stored activity and respiration measurements to an external monitor for display.

129. The method of claim 128 wherein the processing step includes determining delta minute volume measurements based upon the minute volume measurements, creating histograms of the activity and delta minute volume measurements and deriving histogram values from the histograms at spaced apart times.

130. An implantable pacemaker that provides pacing therapy to a heart and monitors, during an extended time period, a progression or regression in congestive heart failure comprising:

a pacer that provides pacing therapy to the heart;

a respiration sensor that generates raw sensor signals indicative of the patient's respiration, wherein a degradation or improvement of the patient's respiration level over time corresponds to an indication of the progression or regression of congestive heart failure;

a processor coupled to the respiration sensor that processes the raw signals to determine respiration measurements and controls the pacer;

a memory coupled to the processor that stores the respiration measurements during the extended time period;

a telemetry circuit that transmits the respiration measurements stored during the extended time period to an external monitor for display; and the processor being programmed to adjust the pacing therapy provided by the pacer responsive to the respiration measurements.

131. The pacemaker of claim 130 wherein the processor is programmed to adjust pacing rate.

132. The pacemaker of claim 130 further including an activity sensor that senses activity of the patient, and wherein the processor stores the respiration measurements when the patient is in at least one active state.

133. An implantable pacemaker for providing pacing therapy to a heart and historical physiological parameter measurements indicative of a progression or regression in congestive heart failure of a patient comprising:

pacing means for pacing the heart;

respiration sensing means for generating sensor signals indicative of the patient's respiration, wherein a degradation or improvement of the patient's respiration level over time corresponds to an indication of the progression of congestive heart failure;

processing means for controlling the pacing means and for processing the raw signals to determine respiration measurements;

storage means for storing the respiration measurements during an extended time period;

telemetry means for transmitting the stored minute volume measurements to an external monitor for display; and the processing means being responsive to the respiration measurements for controlling the pacing means.

134. The pacemaker of claim 133 wherein the processing means controls pacing rate of the pacing means.

135. The pacemaker of claim 133 further including activity sensing means for sensing activity of the patient, and wherein the processing means determines the respiration measurements when the patient is in at least one active state.

136. In an implantable pacemaker, a method of pacing a heart and providing historical physiological parameter measurements indicative of a progression or regression in a patient's congestive heart failure, the method including the steps of:

pacing the heart to provide pacing therapy;

generating raw signals indicative of the patient's respiration, wherein a degradation or improvement of the patient's respiration level over time corresponds to an indication of the progression or regression of congestive heart failure;

processing the raw signals to determine respiration measurements;

storing the respiration measurements during an extended time period;

transmitting the stored respiration measurements to an external monitor for display; and adjusting the pacing therapy responsive to the respiration measurements.

137. The method of claim 136 wherein the extended time period encompasses a plurality of time intervals and wherein the pacing therapy is adjusted during each of the time intervals.

138. The method of claim 136 wherein the adjusting step includes adjusting pacing rate.

139. The method of claim 136 including the further step of sensing activity of the patient, and wherein the processing step is performed when the patient is in at least one active state.

* * * * *